(12) United States Patent
Van der Meeren et al.

(10) Patent No.: US 11,104,895 B2
(45) Date of Patent: Aug. 31, 2021

(54) NON-DESTRUCTIVE SEED GENOTYPING

(71) Applicant: BASF SE, Ludwigshafen am Rhein (DE)

(72) Inventors: Kristof Van der Meeren, Zwijnaarde (BE); Rainhard Koch, Leverkusen (DE); Philipp Ellinger, Leverkusen (DE); Nina Jansen, Leverkusen (DE); Stephen Rae, Zwijnaarde (BE); Martin Clausen, Leverkusen (DE)

(73) Assignee: BASF SE, Ludwigshafen am Rhein (DE)

( * ) Notice: Subject to any disclaimer, the term of this patent is extended or adjusted under 35 U.S.C. 154(b) by 226 days.

(21) Appl. No.: 16/089,957

(22) PCT Filed: Mar. 29, 2017

(86) PCT No.: PCT/EP2017/057438
§ 371 (c)(1),
(2) Date: Sep. 28, 2018

(87) PCT Pub. No.: WO2017/167816
PCT Pub. Date: Oct. 5, 2017

(65) Prior Publication Data
US 2019/0144847 A1 May 16, 2019

(30) Foreign Application Priority Data
Mar. 31, 2016 (EP) .................................... 16163397

(51) Int. Cl.
| | | |
|---|---|---|
| C12N 15/10 | (2006.01) | |
| C12Q 1/6806 | (2018.01) | |
| C12Q 1/6881 | (2018.01) | |
| C12Q 1/6895 | (2018.01) | |
| A01H 1/04 | (2006.01) | |
| A01H 5/10 | (2018.01) | |

(52) U.S. Cl.
CPC .......... *C12N 15/1003* (2013.01); *A01H 1/04* (2013.01); *A01H 5/10* (2013.01); *C12Q 1/6806* (2013.01); *C12Q 1/6881* (2013.01); *C12Q 1/6895* (2013.01); *C12Q 2531/113* (2013.01); *C12Y 301/01003* (2013.01); *C12Y 301/01074* (2013.01); *C12Y 302/01001* (2013.01); *C12Y 302/01004* (2013.01); *C12Y 302/01015* (2013.01)

(58) Field of Classification Search
CPC ................ C12Q 1/6895; C12Q 1/6806; C12Q 2531/113; C12Q 1/6881; A01H 1/04; A01H 5/10; C12Y 301/01001; C12Y 301/01074; C12Y 302/01004; C12N 15/1003
See application file for complete search history.

(56) References Cited

U.S. PATENT DOCUMENTS

| | | |
|---|---|---|
| 7,703,238 B2 | 4/2010 | Deppermann et al. |
| 8,959,833 B2 | 2/2015 | Deppermann et al. |
| 2013/0210006 A1* | 8/2013 | Rapier .................. C12Q 1/686 435/6.11 |

FOREIGN PATENT DOCUMENTS

| | | |
|---|---|---|
| WO | 2004056984 A2 | 7/2004 |
| WO | 2011082316 A2 | 7/2011 |
| WO | 2011119763 A1 | 9/2011 |
| WO | 2011163326 A2 | 12/2011 |
| WO | 2012122156 A2 | 9/2012 |
| WO | 2014071271 A1 | 5/2014 |
| WO | 2014195199 A1 | 12/2014 |

OTHER PUBLICATIONS

International Search Report and Written Opinion for International Patent Application No. PCT/EP2017/057438, dated May 24, 2017, 10 pages.
Chunwongs, et al., "Pre-germination genotypic screening using PCR amplification of half-seeds", Theoretical and Applied Genetics, International Journal Of Plant Breeding Research, vol. 86, Issue 6, 1993, pp. 694-698.
Gao, et al., "Development of a seed DNA-based genotyping system for marker-assisted selection in maize", Molecular Breeding, vol. 22, Issue 3, 2008, pp. 477-494.
Manen, et al., "A fully automatable enzymatic method for DNA extraction from plant tissues", BMC Plant Biology, vol. 5, Issue 1, 2005, 9 pages.
Meru, et al., "A non-destructive genotyping system from a single seed for marker-assisted selection in watermelon", Genetics Molecular Research, vol. 12, Issue 1, 2013, pp. 702-709.
Zheng, et al., "Non-destructive high-throughput DNA extraction and genotyping methods for cotton seeds and seedlings", Biotechniques, vol. 58, Issue 5, 2015, pp. 234-243.

* cited by examiner

*Primary Examiner* — Young J Kim
(74) *Attorney, Agent, or Firm* — Armstrong Teasdale LLP

(57) ABSTRACT

Described herein are methods and means for reliably releasing maternal and/or paternal DNA from single seeds without substantially affecting the subsequent germination of the seeds. The methods are particularly suited for genome analysis of small grain cereals, including wheat. The methods may include enzymatic treatments for improved DNA recovery.

26 Claims, 4 Drawing Sheets
Specification includes a Sequence Listing.

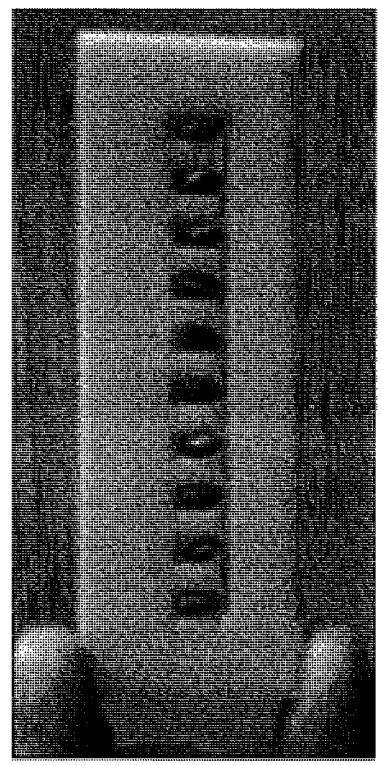
Figure 1
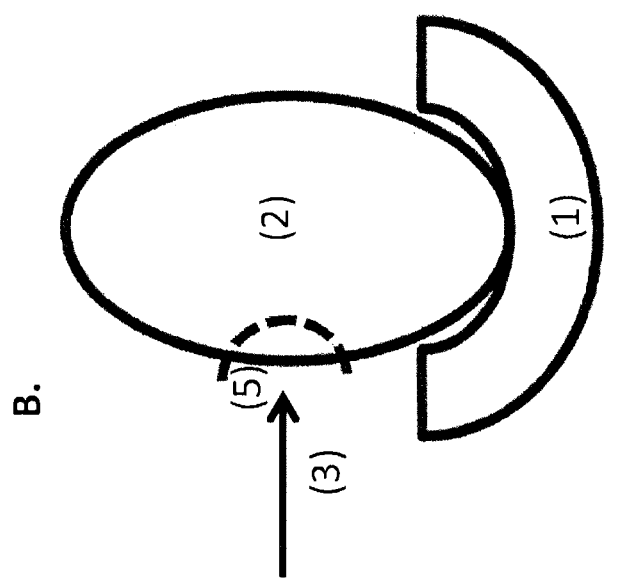
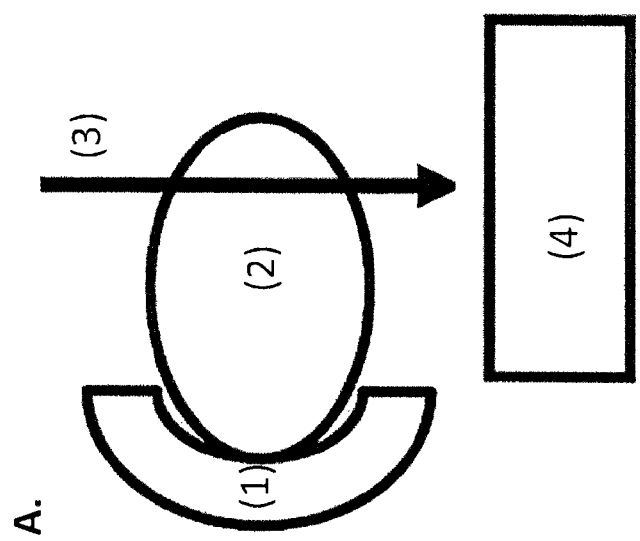
Figure 2

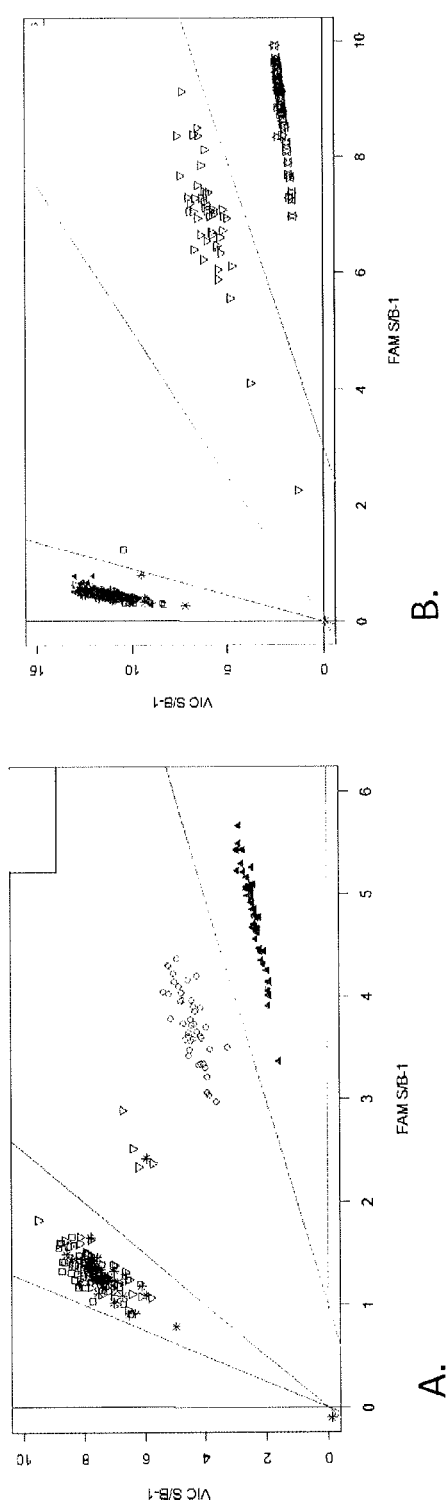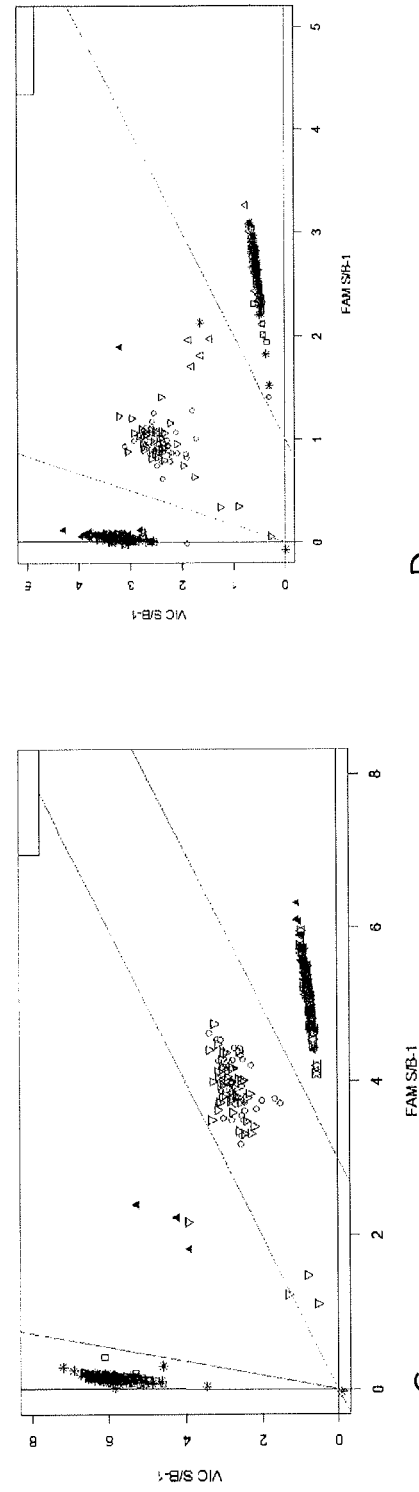
Figure 5

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Taqman  Primer 1 sequence

<400> SEQUENCE: 1
tttccttcta ccatagacga gaaagc                                           26

<210> SEQ ID NO 2
<211> LENGTH: 34
<212> TYPE: DNA
<213> ORGANISM: Artificial Sequence
<220> FEATURE:
<223> OTHER INFORMATION: Taqman  Primer 2 sequence

<400> SEQUENCE: 2
ctggttctct atgtcattat ttgtaaatgt aaat                                  34

<210> SEQ ID NO 3
<211> LENGTH: 15
<212> TYPE: DNA
<213> ORGANISM: Artificial Sequence
<220> FEATURE:
<223> OTHER INFORMATION: Taqman  Probe 1 sequence

<400> SEQUENCE: 3
gcagcacaca cacgt                                                       15

<210> SEQ ID NO 4
<211> LENGTH: 15
<212> TYPE: DNA
<213> ORGANISM: Artificial Sequence
<220> FEATURE:
```

```
<223> OTHER INFORMATION: Taqman Probe 2 sequence

<400> SEQUENCE: 4
gcagcacaca cccgt                                                    15
```

NON-DESTRUCTIVE SEED GENOTYPING

CROSS-REFERENCE TO RELATED APPLICATIONS

This application is the national stage entry of PCT/EP2017/057438, filed on Mar. 29, 2017, which claims the benefit of priority to European Patent Application No. 16163397.9, filed Mar. 31, 2016, each of which is incorporated by reference in its entirety herein.

FIELD OF THE INVENTION

The invention belongs to the field of molecular genome analysis of plants. Methods and means are provided to reliable release maternal and/or paternal DNA from single seeds without substantially affecting the subsequent germination of the analyzed seeds. The method is particularly suited for genome analysis of small grain cereals, including wheat. These methods can be used in various circumstances, including in breeding efforts.

BACKGROUND

Research and development activities in the seeds industry increasingly employ genomic analysis to identify and follow plants with improved and/or desired characteristics. Such characteristics can be obtained by traditional breeding techniques, mutagenesis, transformation etc. Traditionally, genomic analysis during these processes is performed on plantlets or plants, which have grown to a sufficiently developed state to allow the sampling of tissue without harming the plants. After identification of the desired plants, these are allowed to grow further and set seeds, while the undesired plantlets or plants are discarded. Such a process is rather inefficient in terms of using valuable space in greenhouses or other growth facilities.

DNA can also be isolated from individual seeds, but earlier isolation procedures resulted in the destruction of the seeds. Therefore, methods were developed involving the sampling of a part of the seed, without impairing the ability of the embryo to germinate and develop into a plant. DNA analysis is performed on the sampled part or seed chip. The seed chips were isolated using e.g. an automated cutting device or laser beam. Such methods are described in WO2011/082316, WO2011/1 19763, WO2011/163326, WO2012/122156, WO 2014/071271.

U.S. Pat. Nos. 8,959,833 and 7,703,238 describe a high-throughput, non-destructive method for analyzing individual seeds in a population of seeds, the method comprising removing a tissue sample from each of one or more individual seeds in the population using an automated sampler while preserving germination viability of the one or more sampled seeds and analyzing the one or more tissue samples for the presence or absence of one or more characteristics indicative of at least one genetic or chemical trait.

WO2004/056984 entitled "Enzymatic method for the isolation of DNA from plant tissue" describes methods for isolating DNA from plant tissue that utilize a mixture of cell wall degrading enzymes. The invention also relates to kits for isolating DNA from plant tissue wherein the kit comprises a mixture of cell wall degrading enzymes. The description suggests applying the methods to seeds.

Manen et al., 2005 (BMC Plant biology 2005 5.23) describe a fully automatable enzymatic method for DNA extraction from plant tissues.

Zheng et al. (BioTechniques 58:234-243, 2015) disclose methods for non-destructive high-throughput DNA extraction and genotyping of cotton seeds by sampling small amounts of cotyledon tissue of ungerminated seeds, immobilized in modified 96-well plates. Immobilization of seeds in the wells included application of water-soluble glue. The sampled amounts were processed in plate-based format using hydroxide-based DNA extraction process. Aliquots were diluted before PCR based genotyping for SNPs (KASP assays) and simple sequence repeats (SSRs).

WO2014/195199 entitled "Non-disruptive DNA isolation from corn seeds" relates to systems and process for isolating DNA from biological materials such as seeds while retaining a viable seed for further use. The seed from which the DNA is isolated remains viable and is used or discarded based on the DNA analysis of the seed soak solution. The seed soak solution can have substantially all of the confounding maternal DNA from the seed eliminated from the seed soak solutions by employing intact seed pretreatments. This method is deemed particularly useful for maize seed. The methods disclosed have in common the step of exposing the seed endosperm and soaking the seed in a non-disruptive DNA releasing solution. In the examples, the DNA releasing solution is an alkaline solution, comprising 20 mM NaOH.

Despite the availability of several methodologies for seed genotyping in a non-destructive manner, there remains a need for alternative and/or improved, more reliable and more robust technology for isolating DNA (including paternal DNA) from seeds, particularly cereal seeds such as wheat seeds.

The current invention provides such methods as described in the various embodiments, examples and claims hereinafter.

SUMMARY OF THE INVENTION

In a first embodiment, a method is provided for isolating nucleic acids, including DNA from small grain cereal seed and/or for analyzing a population of small grain cereal seeds comprising the steps of a. exposing the endosperm of at least one individual seed of the population, optionally by at least partial removal of the cereal seed end opposite the micropylar end of the seed;

b. incubating the seed in an aqueous solution for an amount of time sufficient to release nucleic acids, such as between 15 min to 4 hr or between 30 min to 2 hr, including DNA from the seed and forming a solution comprising nucleic acids such as DNA, optionally comprising one or more carbohydrate degrading enzyme such as a cell wall degrading enzyme, an ester hydrolyzing enzyme such as an esterase, a cutinase or a lipase, or an amylase, optionally one or more enzymes selected from pectinase, cellulase, xylanase, amylase or *Candida antartica* lipase B.

c. optionally concentrating and/or purifying the nucleic acids such as DNA from the soaked solution;

d. optionally analyzing the solution or the nucleic acids, including DNA, to detect the presence of a nucleic acid of interest; and e. optionally, growing a plant from the seed.

The population of seeds can be sorted into subpopulations of seeds wherein the DNA of interest could be detected or not detected, or can be sorted into subpopulations of seeds according to the homozygous, hemizygous, heterozygous or azygous occurrence of the DNA of interest. The DNA can be of maternal origin and/or paternal origin.

In an alternative embodiment, the micropylar end of the seed may be covered with a protective coat, such as a silicon based sleeve or an non-toxic water based dispersion which can be used for fixation and for protection such as an aliphatic polycarbonate ester-polyether polyurethane dispersion, including as Impranil® DNL or a water soluble glue such as Helping Hand Carpenter's Glue. The non-covered end of the seed can be treated with an abrasive, such as sand or glass beads, until the endosperm is exposed or can be treated with sand paper or file until the endosperm is exposed, or can be removed mechanically e.g. by using a knife or nail clipper.

In yet another embodiment, the invention provides a method for analyzing a population of small grain cereal seeds comprising the steps of
a. exposing the endosperm of at least one individual seed of the population by partial removal of the cereal seed end opposite the micropylar end of the seed;
b. incubating the seed in an aqueous solution comprising one or more enzymes selected from pectinase, cellulose, xylanase, amylase or *Candida antartica* lipase B, for an amount of time sufficient to allow release and/or diffusion of nucleic acids from the seed and a solution comprising nucleic acids is formed;
c. optionally concentrating and/or purifying the nucleic acids from the soaked solution;
d. analyzing the solution or the nucleic acids to detect the presence of a nucleic acid of interest; and
e. optionally, growing a plant from the seed.

It is also an embodiment of the invention to provide a method for isolating maternal DNA from small grain cereal seeds comprising the steps of
a. incubating the seed in an aqueous solution for an amount of time sufficient to allow release and/or diffusion of nucleic acids from the seed, thereby forming a solution comprising nucleic acids wherein the aqueous solution comprises one or more carbohydrate degrading enzyme such as a cell wall degrading enzyme, ester hydrolyzing enzymes such as an esterase, a cutinase or a lipase, or an amylase, optionally one or more enzymes selected from pectinase, cellulase, xylanase, amylase or *Candida antartica* lipase B;
b. optionally concentrating, amplifying and/or purifying the nucleic acids from the soaked solution;
c. optionally analyzing the solution or the nucleic acids to detect the presence of a nucleic acid of interest.

BRIEF DESCRIPTION OF THE DRAWINGS

FIG. 1. Schematic representation of use of a water jet stream to remove the end of a small grain cereal seed opposite the micropylar end or to expose the endosperm. A. Side view B. Top view. (1) Fixation means (2) small grain cereal seed (3) water jet (4) catch basin (5) exposed endosperm.

FIG. 2. Example of a pre-formed mould with depressions that are more long than wide, for holding small grain cereal seeds.

FIG. 5 represents 4 exemplary plots of results of Taqman® assays performed on DNA samples extracted as described in the Examples from seeds harvested from seven parental wheat lines and from F1 (first filial generation) seeds harvested from crosses between the varieties. A. Marker 1; B. Marker 2; C. Marker 3; and D. Marker 4.

DETAILED DESCRIPTION OF THE INVENTION

Figure 3:
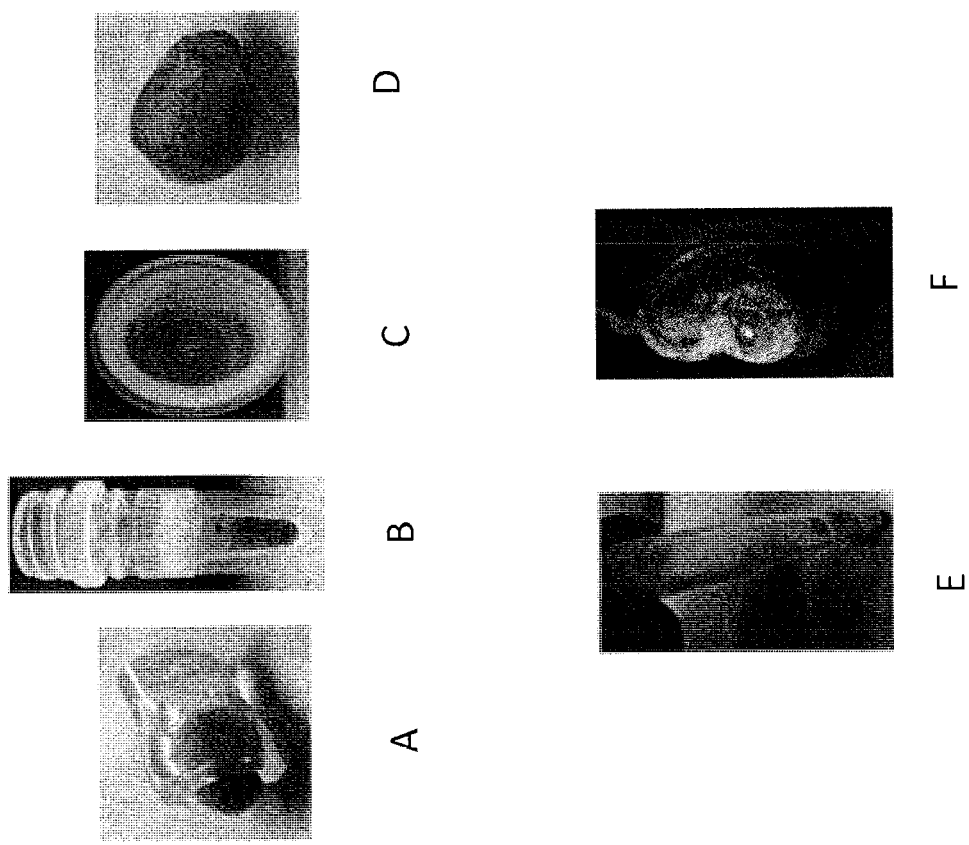
FIG. 3. A. Wheat seed protected by silicon sleeve exposing the seed end having brush or beard. B. Protected wheat seed in tube with glass beads. C. Wheat seed after glass bead treatment. D. Treated wheat seed removed from sleeve. E. Wheat seed with micropylar end protected by Impranil®. F. Wheat seed after protection with Impranil® and treatment with glass beads.

The current invention is based upon the observation that in cereal seeds, the seed end opposite of the micropylar end, where the embryo resides, can be removed, at least partially, thereby exposing the endosperm and other tissue layers surrounding the endosperm, allowing nucleic acids such as DNA to diffuse into a solution in which the seed is soaked, without impairing the viability and subsequent germination ability of the seed. The nucleic acids, including DNA can be analysed using techniques common in the art, optionally after concentration, amplification and/or purification. Thus, a method is provided allowing non-destructive seed genotyping.

In wheat seeds, the end opposite of the micropylar end of the seed, can easily be recognized since in this region, hairy projections are present, which is commonly referred to as brush or beard. It has been found that manipulations in this region to remove the outer layers of the seed (pericarp, seed coat, hyaline layer, aleurone layer) and/or expose the endosperm have little or no influence on the germination of the seeds thereafter. Conveniently, the end of the cereal seed, particularly wheat seed, can be scratched with a file, mechanically removed, e.g. with a knife or nail clipper or treated with an abrasive material, until the outer layers in that region are removed and the endosperm is exposed. At least up to one fifth of the seed end opposite the micropylar end can be removed e.g. by filing or scratching or treating with an abrasive material. It should however be noted that in case of partial removal of the outer layers of the seeds to expose the endosperm, such as by making a hole through the outer layers to reach the endosperm, the restrictions are not as strict as in the case of complete removal. The only requirement is that the treatment to expose the endosperm does not result in damage to the embryo. This could be achieved by removing only a small portion of the outer layers to expose the endosperm and this can be done preferably around the centre, where the seed is widest, or in the half of the seed opposite the mycropylar end.

Thus, in a first embodiment, a method is provided for analyzing a population of small grain cereal seeds comprising the steps of exposing the endosperm of at least one individual seed of said population by at least partial removal of the cereal seed end opposite the micropylar end of the seed and incubating the seed in an aqueous solution for an amount of time sufficient to allow release of nucleic acids from the seed, thereby forming a solution comprising nucleic acids followed by analyzing said solution or said nucleic acids to detect the presence of a nucleic acid of interest. Optionally, the nucleic acids may be concentrated, amplified and/or purified from the soaked solution. Also optionally, a plant may be grown from said seed.

The nucleic acid or DNA isolated from the seeds may be analysed for the presence of a particular transgenic nucleic acid or DNA, or for the detection of the presence of a particular allele or marker in the DNA and thus in the corresponding seeds. The seeds may then be divided in subpopulation of seeds wherein the particular DNA, allele or marker has been detected and those seeds wherein the particular DNA, allele or marker has not been detected. Other methods of creating subpopulation could be based on the detection of the DNA, allele or marker in homozygous, hemizygous or heterozygous or azygous state. Unwanted subpopulations can then be discarded.

In plants, the pericarp tissue originates or derives from the mature ovule wall, which is maternal tissue and comprises only maternal DNA. Other tissues of the seed underneath the seed coat are of both paternal and maternal origin and comprise both paternal and maternal DNA. Whereas the determination of maternal DNA has important applications; including the determination of maternal lineage, the characterization of line genetic (dis)similarities etc., it is also important to be able to determine the paternal lineage, particularly in hybrid plants. Therefore, it is important to be able to isolate DNA from the tissues of the seeds, such as small grain cereal seeds, which are located underneath the seed coat.

It has further been observed by the inventors that nucleic acid or DNA recovery from the seeds wherein the end opposite to the micropylar end of the cereal seed has been partially removed, or where the endosperm has been exposed in any other manner, can be improved by incubating the seeds in an aqueous solution comprising one or more carbohydrate degrading enzyme such as cell wall degrading enzymes, ester hydrolysing enzymes and/or amylases.

As used herein "a cell wall degrading enzyme" refers to a hydrolytic enzyme which can catalyse depolymerisation of polymers found in plant cell wall, including polysaccharides found in plant cell walls. Plant cell walls are heterogeneous structures, composed of polysaccharides, proteins and aromatic polymers. The composition and structure of the cell wall differ significantly among plant lineages, but all contain cellulose microfibrils embedded in a matrix of pectin, hemicellulose, lignin and structural proteins. Additional polysaccharides contained in cell walls include xyloglucan, xylan, glucuroarabinoxylan.

A convenient source of cell wall degrading enzymes are pathogenic and/or saprophytic fungi. Cell wall degrading enzymes produced by phytopathogenic fungi focus on decomposition of cellulose, xylan and pectin. Enzymes that are capable of hydrolytically cleaving glycosidic bonds in oligo- or polysaccharides are generally referred to as glycoside hydrolases.

Cellulose degrading enzymes catalyse the hydrolysis of cellulose, involving the action of two types of cellulases: exoglucanases (cellobiohydrolases) or endocellulases/endoglucanases (endo 1,4-glucanases) followed by a -glucosidase that hydrolyzes the soluble cellodextrin oligomers into glucose. The strict separation of cellulases into endo and exocellulases is an simplification since cellulases have evolved overlapping modes of action.

Hemicellulose degrading enzymes degrade hemi-cellulose, a term used to describe non cellulosic polysaccharides of the cell wall, comprising xyloglucans, xylans and galactomannans. The backbone of xyloglucans can be degraded by both specific or nonspecific endo 1,4-glucanases, and endo 1,4-glucanases with xyloglucanase activity can be found in fungi. Endo-1,4-β-xylanases cleave the glycosidic bonds in the xylan backbone. The mannan degrading enzymes comprise -mannanase (1,4- -D-mannan mannohydrolase) and -mannosidase (1,4- -D mannopyranoside hydrolase). Complete depolymerisation of hemicellulose may further involve α galactosidases, α-arabinosidases, β-galactosidases and β-glucuronidases.

Pectin can be degraded by polygalacturonidases, or can be cleaved by a nonhydrolytic reaction called β-elimination which uses pectin lyases and pectate lyases.

Cutinases are serine esterases acting on the carboxylic ester bond of cutin (a polyester composed of hydroxyl and hydroxyepoxy fatty acids. Lipase B also belongs to the class of serine esterases.

Amylases are enzymes (glycoside hydrolases) that hydrolyze starch into sugars by acting on the α-1,4-glycosidic bonds. α-amylases break down long-chain carbohydrates, ultimately yielding maltotriose and maltose from amylase, or maltose, glucose and dextrin from amylopectin. β-amylase catalyzes the hydrolysis of the second α-1,4 glycosidic bond from the non-reducing end, cleaving of two glucose units (maltose) at the time. γ-amylase cleaves α(1-6) glycosidic linkages, as well as the last α(1-4) glycosidic linkages at the nonreducing end of amylase and amylopectin, yielding glucose.

Particularly suited enzymes for methods of invention include pectinase, such as pectinase from *Aspergillus niger*; cellulase such as cellulase from *Trichoderma reesei* ATCC 26921; xylanase, such as xylanase from *Trichoderma longibrachiatum*; amylase, such as amylase from *Bacillus licheniformis*, and *Candida antartica* lipase B, such as the *Candida antarctica* lipase B recombinantly produced in *Aspergillus oryzae*. The exemplified enzymes are all commercially available, and can be purchased e.g. from Sigma Aldrich.

In one embodiment, the seeds are treated with a mixture of pectinase, cellulose, xylanase, amylase and lipase B from *Candida antartica*.

Typical enzyme concentrations used vary around 20 mg/ml, but other concentrations can be used including between 1 to 100 mg/ml.

In the methods according to the invention, the seeds from which the endosperm has been exposed are incubated in an aqueous solution for an amount of time sufficient to release nucleic acids from the seed and forming a solution comprising nucleic acids. As used herein "for an amount of time sufficient to release nucleic acids from the seed" refers to a time sufficient for nucleic acids, such as DNA, to diffuse from the seed and being detectable in the solution. Typically the time ranges from 10 minutes to 4 or 5 hours, particularly from 30 minutes to 2 hours. It will be clear that the time required for the nucleic acids, including DNA to be released from the seed may vary from plant species to plant species and may even vary between plant varieties of the same species. Furthermore, the time needed or sufficient to recover DNA from the seeds, as well as the amount of recovered DNA may vary depending on the presence or absence and/or concentration of enzymes in the solution in which the seeds are incubated. The time of incubation in the presence of enzymes, may, depending also upon the concentration of the enzymes, influence the subsequent germination ability of the treated seeds.

The aqueous solution used for incubating the seeds may be a buffered solution, such as a buffer containing 10 mM sodium phosphate, at pH 7.3. The aqueous solution may further contain a detergent such as 1% sodium dodecylsulfate. The aqueous solution may also contain sodium citric acid, e.g. in a concentration of 50 mM. Further ingredients may be added to inactivate or inhibit DNases. It will be clear that other buffer solutions, or other detergents, or other additional ingredients, such as e.g. citric acid, may be employed and the use thereof is well known to the person skilled in the art. In one embodiment, the aqueous solution is a neutral solution, with a pH around 7, such as between 6.5 and 7.5.

In one embodiment (regardless of whether the method involve enzymatic treatment as herein described or not) the endosperm of the seeds may be exposed using a water jet, e.g. to remove outer layers of the seed(s), to remove the end opposite to the mycropylar end of the seeds, or to drill a hole into the seed. The use of a water jet is advantageous since particles or parts of the seeds which are removed from the seeds may be washed away by the water jet thereby reducing the risk of cross-contamination between different seeds. Furthermore, this method does not involve the use of a solid tool, such as clipping device, file, drill, dremel or the like which can carry cross-contaminating material from one seed to another. The thermal and mechanical burden imposed by a water jet is also rather small, so that the seeds, seeds surfaces (as well as removed seeds parts) remain intact and the germination capacity is retained. Moreover, due to the relatively small forces which are used, the design of a holding device to hold the seeds can be simplified.

Water jet cutting devices are (commercially) available and can be purchased e.g. from Flow International Corporation (www.flowwaterjet.com) or KMT Waterjet Systems Inc (www.kmtwaterjet.com) to name but a few suppliers. In one embodiment, the water jet may have a pressure of around 6000 bar, a jet diameter of 0.1 mm and a cutting width of 250 μm.

To remove the end opposite of the mycropylar end of a seed by a water jet, or otherwise expose the endosperm, it may be advantageous to fix the seed in a particular orientation (schematically represented in FIG. 1). Such fixing of the seed could be achieved e.g. by underpressure in a depression in holding material. After the treatment with the water jet is finished the seed can then be released, by removing the underpressure or by overpressure. Other manners of orienting and holding seeds during water jet treatment may be applied, including mounting the seeds in pre-formed moulds with depressions that are more long than wide, for small grain cereal seeds (FIG. 2). It is even expected that for making a hole in the middle of small grain cereal seed, no pre- or forced orientation of the seeds may be needed.

The methods of the invention can be adapted to be performed in an automatic or semi-automatic manner to increase the throughput of the analysis. To this end, the seeds may be pre-fixed in a particular orientation, e.g. using a method as described above, and treated to expose the endosperm, e.g. using a water jet as described above, released and transferred into a multi-well plate where the treated seeds are incubated in the DNA releasing solution as described elsewhere in the application, optionally including enzymes as described herein. From thereon, the liquids containing the released DNA can be automatically transferred and analysed according to any method applicable in the art, while the seeds are dried, optionally after rinsing, and stored pending the outcome of the analysis.

The, at least partial, removal of one end of the seed opposite the micropylar end of the seed can also be conveniently achieved by coating the micropylar end (comprising the embryo) prior to subjecting the seed to abrasive conditions, such as treating with abrasive materials. Abrasive materials are well known in the art and include calcite (calcium carbonate), emery, diamond dust, novaculite, pulice, sand, corundum, garnet, sandstone, Tripoli, powdered feldspar, staurolite, borazon (cubic bron nitride), ceramic aluminium oxide, ceramic iron oxide, dry ice, glass powder, steel abrasive, silicon carbide (carborundum) zirconia alumina, boron carbide, slags and others.

The coating of the micropylar end of the can be achieved by inserting the seed with the micropylar end into a tightly fitting silicon sleeve. In the case of wheat seed, the opposite end with the beard or brush is still exposed to the at least partial removal of outer seed layers by the abrasive material.

The coating of the micropylar end of the can also be achieved by coating the micropylar end of the seed, such as a wheat seed, with non-toxic coating material, including waxes, glues, varnishes or lacquers. One example of coating material could be wood glue or carpenter's glue or yellow glue, preferably water-soluble, non-toxic wood glue. Another of coating material is represented by aqueous polyurethane dispersions.

As used herein polyurethane is an addition product of at least one polyisocyanate component and at least one polyol component. The polyisocyanate component generally comprises at least one diisocyanate. The isocyanate component may additionally also comprise isocyanates of higher functionality, for example triisocyanates or oligomeric isocyanates having on average more than two and preferably three or more isocyanate groups. The polyol component generally comprises at least one diol. The polyol component may further comprise higher-functionality polyols or oligomeric polyols having on average more than two OH groups, preferably three, four or more OH groups. The polyurethane can additionally contain urea groups based on the reaction of amines with isocyanates.

Aqueous polyurethane coatings are water based dispersions that have outstanding performance properties, containing no volatile organic compounds making them highly suitable in several coating applications. Aqueous polyurethane dispersions are made in at least two stages: the prepolymer formation and the dispersion formation. In the first stage, an isocyanate terminated prepolymer is prepared by combining chemical reactants including at least one isocyanate reactive compound capable of imparting some hydrophilicity to the material, neutralizing the isocyanate reactive group with a neutralizing agent having a suitable organic counter ion, and optionally reacting at least a portion of the isocyanate end groups of the isocyanate terminated prepolymer with a chain terminating agent. In the second stage, the aqueous polyurethane dispersion is prepared by dispersing the prepolymer in water to provide an aqueous-based dispersion, and chain extending the prepolymer with a chain extending agent. The molecular weight of polyurethane polymer contained within the aqueous polyurethane dispersion may be controlled by adding at least one chain terminating agent to the reaction mixture and/or monitoring the amount of amine from the neutralizing agent to acid functional groups from the isocyanate reactive compound. The isocyanate terminated prepolymer is prepared from a reaction mixture comprising at least one diisocyanate, at least one difunctional polyol, at least one isocyanate reactive compound, a neutralizing agent, optionally a chain terminating agent, optionally a catalyst, and optionally a solvent. The reaction occurs using a stoichiometric excess of the at least one diisocyanate relative to the at least one difunctional polyol and the at least one isocyanate reactive compound to produce an oligomer which may contain urethane and urea functional groups.

The dispersions when dried, are hard but at the same time still allow the seed to germinate. Preferably, the dispersion has specific film parameters comprising a tensile strength of 25-150 MPa (megapascals) and a 100% modulus of 3-30 MPa. Even more preferably the specific film parameters are a tensile strength of 35-70 MPa and a 100% modulus of 4-20 MPa. Tensile strength is the force placed on the sample divided by the cross-sectional area of the sample, tensile strength is measured in units of force divided by units of area, usually $N/cm^2$, tensile strength can also be measured in psi (1 $N/cm^2$=1.45 psi). Ultimate tensile strength is the force needed to stretch a material until it breaks. Strength can also be measured in megapascals (MPa). The conversion is 1 MPa=100 $N/cm^2$. The modulus is a measure how well a certain material resists deformation. 100% modulus is the force needed to stretch the material to twice its original dimensions.

In a particular preferred embodiment the aqueous polyurethane dispersion used is a dispersion of Impranil® DLU. The latter aqueous polyurethane is an anionic aliphatic polyester-polyurethane dispersion. Impranil® DLU is suitable for the formulation of textile coatings and also for coating and finishing of various technical articles such as outer wear, bags, luggage, fashion shoe leather uppers, belts, hoses, glass fabrics and fabrics made from synthetic fibers.

In yet another particular embodiment the aqueous polyurethane dispersion used for coating seed is a dispersion of Impranil® XP 2611. The latter aqueous polyurethane is an anionic aliphatic polyester-polyurethane dispersion. Impranil® XP 2611 is suitable for the formulation of textile coatings and also for coating and finishing of various technical articles such as outer wear, bags, luggage, fashion shoe leather uppers and the like. Impranil® XP 2611 has thus far never been considered for seed coating purposes.

According to another embodiment of the invention, the aqueous polyurethane dispersion consists of aliphatic isocyanates and polyols.

Although not necessary, the polyurethane coating may be removed from the seed, either after treating with the abrasive material, or after the time required for the nucleic acid to have dissolved from the treated seed with at least partially exposed endosperm. Removal may be achieved mechanically. Removal of the polyurethane coating may also be achieved by enzymatic treatment, such as treatment with lipases or cutinases. Removal of wood glue can be achieved by dissolution in water.

The protective coat should cover at least the micropylar end of the seed, preferably at least half the seed, particularly about ⅘ of the seed.

It has been observed that at least maternal DNA can also be released from the pericarp tissues of the small grain cereal seeds, such as wheat, without abrasion by treatment with enzymes only, as described elsewhere in this application. Thus in an alternative embodiment, the invention provides a method for isolating maternal DNA from small grain cereal seeds comprising the steps of
  a. incubating the seed in an aqueous solution for an amount of time sufficient to allow release of nucleic acids from the seed, thereby forming a solution comprising nucleic acids wherein said aqueous solution comprises one or more carbohydrate degrading enzyme such as a cell wall degrading enzyme, an ester hydrolyzing enzymes such as a cutinase, an esterase or lipase, or an amylase, optionally one or more enzymes selected from pectinase, cellulase, xylanase, amylase or *Candida antartica* lipase B;
  b. optionally concentrating, amplifying and/or purifying the nucleic acids from the soaked solution;
  c. optionally analyzing said solution or said nucleic acids to detect the presence of a nucleic acid of interest; and
  d. optionally, growing a plant from said seed.

The DNA in the solutions according to the invention, may be concentrated and/or purified in any way known in the art.

The isolated DNA may further be subjected to any of the usual DNA analysis techniques including PCR analysis, real-time quantitative PCRs, Taqman® assays, Kasp™ assays, as well as other DNA analysis techniques. Potential applications include the detection of single nucleotide polymorphisms, copy number analysis, copy number variations but also whole genome amplification and the like.

The methods of the invention can be performed manually, but can also be automized or applied in a semi-automatic manner.

It is expected that the methods according to the invention can be applied to any seeds of any plant, whether dicotyledonous or monocotyledonous. It is further expected that the methods according to the invention will be particularly suitable for the non-destructive genome analysis for seeds of monocotyledonous plants, particularly seeds of small grain cereals including wheat, rye, sorghum, rice, oats or millet, particularly for wheat.

The term "wheat", "wheat seed" or "wheat plant" as herein used means plant species of the genus *Triticum* or plants resulting from crosses with plants of the genus *Triticum*, particularly plant species of the genus *Triticum* or plants resulting from crosses with plants of the genus *Triticum*, which are used in agriculture for commercial purposes, and particularly preferably *Triticum aestivum* or *Triticum durum*. Plants obtained from such a cross include triticale plants.

As used herein "comprising" is to be interpreted as specifying the presence of the stated features, integers, steps or components as referred to, but does not preclude the presence or addition of one or more features, integers, steps or components, or groups thereof.

It must be noted that as used herein, the terms "a", "an", and "the", include singular and plural references unless the context clearly indicates otherwise, i.e., such terms may refer to "one", "one or more" or "at least one". Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Recombinant DNA techniques or molecular analyses if needed may be carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

The sequence listing contained in the file named "BCS16-2005_ST25-WO1.txt", which is 1 kilobytes (size as measured in Microsoft Windows®), contains 4 sequences SEQ ID NO: 1 through SEQ ID NO: 4, is filed herewith by electronic submission and is incorporated by reference herein.

Throughout the description and Examples, reference is made to the following sequences represented in the sequence listing:

SEQ ID No 1: nucleotide sequence of Taqman® Primer 1 sequence
SEQ ID No 2: nucleotide sequence of Taqman® Primer 2 sequence
SEQ ID No 3: nucleotide sequence of Taqman® Probe 1 sequence
SEQ ID No 4: nucleotide sequence of Taqman® Probe 2 sequence

EXAMPLES

Example 1

Comparison of DNA Isolated from Various Single Wheat Seeds After Abrasion, with or Without Enzymatic Treatment Seeds of a first wheat variety (Variety 1), a second wheat variety (Variety 2) and F1 seeds resulting from a cross between both varieties were used to isolate DNA from single seeds in a non-destructive manner. Seeds were either abraded only, or both abraded and enzymatically treated. A single nucleotide polymorphism in a genomic region differing between Variety 1 and 2 was assayed to determine whether the isolation method released both maternal and paternal DNA (in the F1 seeds).

The end of wheat seed with the brush or beard was removed through abrasion with a file (such as a nail file). Up to one fifth of the total seed volume can be removed. After the abrasion, it is best that the white starch is exposed.

The seed was placed in Eppendorf tubes with the abraded part upwards. The seed was incubated in a buffer solution (10 mM sodium phosphate, 1% SDS and 50 mM sodium citric acid adjusted to pH 7.3) to release the gDNA. For the DNA isolations involving enzymes, abraded seeds were treated with the above mentioned buffered solution comprising Pectinase from *Aspergillus niger* (#P4716-25KU)
Cellulase from *Trichoderma reesei* ATCC26921 #(C27-30-SOML)
Xylanase from *Trichoderma longibrachiatum* #(X2629-100G)
Amylase from *Bacillus licheniformis* (#A3403-1MU)
Lipase B *Candida antarctica*, recombinantly produced by *Aspergillus oryzae* (#62288-250MG-F)

All enzymes were purchased from Sigma Aldrich (order numbers between brackets).

Enzymes which were formulated as powders were dissolved in 10 mM sodium phosphate buffer, pH 7.0. Each enzyme was dissolved in this buffer with a concentration of 100 mg enzyme/ml buffer. The enzymes were dissolved separately. Liquid enzymes were used as they were delivered.

le;2qThe enzyme mixture contained equal volumes all five enzyme solutions. E.g. if 2 ml of enzyme mix was needed 400 µl of each liquid enzyme and 400 µl of each freshly dissolved enzyme were mixed.

le;2qSeeds were soaked with 200 µl of buffer and 16 µl of enzyme mixture were added to the seed for enzyme treated seed samples. The seeds were incubated in the enzyme buffer mix at room temperature and were shaken in a thermomixer with a speed of 1100 rpm. The treatment time varied from 0.5 h, 1 h or 2 h.

le;2qAfter the incubation, the buffer into which the DNA was released was removed. This solution can be stored at −20° C. Seeds were stored at 4° C. until used forgermination.

le;2qStored buffer solutions with DNA were purified using the "Charge Switch® gDNA Plant kit" from Life technologies slightly adapted in the first step:

le;2qChargeSwitch Precipitation Buffer (N5) was chilled on ice

Reagent A ws prepared as described in the manual

200 µl incubation liquid+1000 µl Lysis Buffer (incl. Reagent A) was mixed

2 µl RNase A was added

100 µl SDS as provided by the kit was added

The solution was incubated for 5 min at room temperature

400 µl ChargeSwitch Precipitation Buffer (N5) was added and mixed

The samples were centrifuged for 5 minutes at room temperature

The clear solution was pipetted into a new 2 ml reaction tube

Binding to magnetic beads, washing and elution of DNA from magnetic beads was performed as described in the manufacturers, manual. The typical eluate volumes of about 150 µl were dried in a SpeedVac until the volume was concentrated to about 30 µl.

TaqMan® PCR was performed according to standard conditions (a sample volume of 4.4 µl with a DNA concentration between 20 and 45 ng/µl) using the following primers and probes designed to detect a Single Nucleotide Polymorphism [A/C] between DNA from Variety 1 and DNA from Variety 2:

```
Primer 1:
                                        (SEQ ID No. 1)
5'-TTTCCTTCTACCATAGACGAGAAAGC-3'

Primer 2:
                                        (SEQ ID No. 2)
5'-CTGGTTCTCTATGTCATTATTTGTAAATGTAAAT-3'

Probe 1 (detects the "A-allele"):
                                        (SEQ ID No. 3)
5'-GCAGCACACACACGT-3' carrying a VIC fluorophore Probe 2 (detects the "C-allele"):
                                        (SEQ ID No. 4)
5'-GCAGCACACACCCGT-3' carrying a FAM fluorophore
```

The experimental set-up contained DNA samples from seeds of each variety and the F1 generation, isolated with or without enzymatic treatment, positive control samples of DNA isolated from leaves of each variety and the F1 generation from a cross between both varieties using the ChargeSwitch DNA isolation kit, as well as no template controls.

Figure 4:
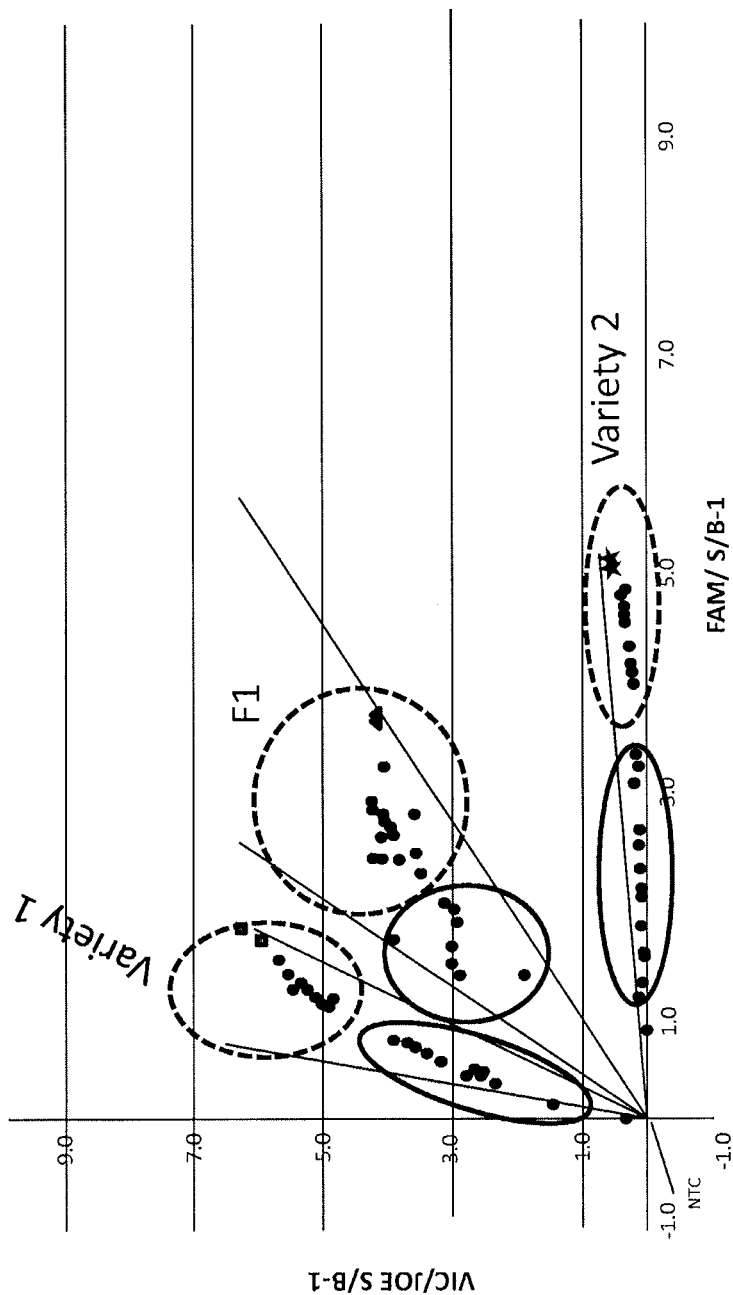
FIG. 4 is a plot of the results of a Taqman® assay performed on DNA samples extracted as described in the Examples from seeds harvested from variety 1, from variety 2 and from F1 (first filial generation) seeds harvested from a cross between Variety 1 and Variety 2. Fluorescence readings (•) of the DNA samples untreated with enzymes cluster within the solid drawn oval, whereas the DNA samples treated with enzymes cluster within the oval drawn in dotted lines. Fluorescence reading of DNA samples prepared from leave material (positive control) are represented by ■ (Variety 1) * (Variety 2) ▲ (F1 seeds).

FIG. 4 shows the results from the TaqMan® assay. As evidenced by the detection of amplification signals around the 45 degree slope for DNA samples from F1 seeds, both isolation methods (with and without enzymatic treatment) resulted in samples containing paternal and maternal DNA. The DNA samples from the enzymatically treated seeds clustered closely together with the positive controls, indicative of a better amplification result and better and/or more concentrated DNA release from the seeds.

The treated seeds were then tested for germination by incubating the treated seeds on a layer of filter paper (thickness of a few mm) soaked with tap water until saturation, and incubation at room temperature. The evaporated water was replaced based on the weight loss. 14 out of 15 seeds treated by abrasion and enzyme treatment of the variety 1 germinated; 13 out of 15 seeds treated by abrasion and enzyme treatment of the variety 2 germinated; 5 to 8 (depending on experiment) of the F1 generation germinated. It is however expected that the seeds of the F1 generation were of lesser quality.

Example 2

Validation of the DNA Analysis Method Including Enzymatic Treatment for Several Single Wheat Seeds of Different Parental Lines and Hybrids Thereof for Different Markers Seeds of seven wheat lines and F1 seeds resulting from crosses between these lines varieties were used to isolate DNA from single seeds in a non-destructive manner using the enzymatic treatment method as described in Example 1. Single nucleotide polymorphisms in a genomic region differing between the varieties were assayed to determine whether the isolation method released both maternal and paternal DNA (in the F1 seeds).

The 7 different parental wheat lines and F1 progeny thereof were analyzed using 12 different sets of primers and probes for detection of 12 different SNPs which can be detected/discriminated in the parental lines.

Taqman® PCRs were performed according to standard conditions using 12 different sets of primers and probes for detection of 12 different SNPs which can be detected/discriminated in the parental lines.

FIG. 5 shows the results from the Taqman® assays for 4 separate sets of primers and probes, as examples. In each case amplification signals were detected around the 45 degree slope for DNA samples from F1 progeny seeds.

The invention claimed is:

1. A method for isolating nucleic acids from small grain cereal seed and/or analyzing a population of small grain cereal seeds comprising the steps of
   a. exposing the endosperm of at least one individual seed of said population by at least partial removal of the cereal seed end opposite the micropylar end of the seed;
   b. incubating the seed in an aqueous solution comprising one or more enzymes selected from the group consisting of pectinase, cellulase, xylanase, amylase, and lipase for an amount of time sufficient to allow release of nucleic acids from the seed, thereby forming a soaked solution comprising nucleic acids;
   c. optionally concentrating, amplifying and/or purifying the nucleic acids from the soaked solution;
   d. analyzing said soaked solution or said nucleic acids to detect the presence of a nucleic acid of interest; and
   e. optionally, growing a plant from said seed.

2. The method according to claim 1, wherein said population of seeds is sorted into subpopulations of seeds wherein said nucleic acid of interest could be detected or not detected.

3. The method according to claim 1, wherein said population is sorted into subpopulations of seeds according to the homozygous, hemizygous, heterozygous or azygous occurrence of said nucleic acid of interest.

4. The method according to claim 1, wherein said nucleic acid of interest is DNA.

5. The method according to claim 1, wherein said nucleic acid of interest is paternal DNA.

6. The method according to claim 1, wherein said nucleic acid of interest is maternal DNA.

7. The method according to claim 1, wherein said amount of time of incubating in a solution is between 15 min and 4 hr.

8. The method according to claim 1, wherein said amount of time of incubating in a solution is between 30 min and 2 hr.

9. The method according to claim 1, wherein the micropylar end of the seed is covered with a protective coat.

10. The method according to claim 9 wherein the micropylar end of the seed is contained within a sleeve.

11. The method according to claim 10, wherein the sleeve is a silicon based sleeve.

12. The method according to claim 9, wherein the micropylar end of the seed is covered with a non-toxic coating material.

13. The method according to claim 12, wherein the non-toxic coating material is a wax, a glue, a varnish or a lacquer.

14. The method according to claim 9, wherein the micropylar end of the seed is covered with wood glue or carpenter's glue or yellow glue.

15. The method according to claim 9, wherein the micropylar end of the seed is covered with an aqueous polyurethane.

16. The method according to claim 15, wherein the aqueous polyurethane is an aliphatic polycarbonate ester-polyether polyurethane dispersion.

17. The method according to claim 1, wherein the non-covered end of the seed is treated with an abrasive until the endosperm is exposed.

18. The method according to claim 17, wherein the abrasive is sand or glass beads.

19. The method according to claim 1, wherein the cereal seed end opposite the micropylar end of the seed is treated with sand paper or a file until the endosperm is exposed.

20. The method according to claim 1, wherein the cereal seed end opposite the micropylar end of the seed is mechanically removed.

21. The method according to claim 20, wherein the cereal seed end opposite the micropylar end of the seed is mechanically removed by a knife or nail clipper.

22. The method according to claim 1, wherein the endosperm is exposed by treatment with a water jet stream.

23. The method according to claim 1 wherein the cereal seed is a wheat seed and the seed end opposite the micropylar end of the seed is the end having a brush or beard.

24. A method for analyzing a population of small grain cereal seeds comprising the steps of
   a. exposing the endosperm of at least one individual seed of said population by partial removal of the cereal seed end opposite the micropylar end of the seed;
   b. incubating the seed in an aqueous solution comprising one or more enzymes selected from pectinase, cellulase, xylanase, amylase or *Candida antartica* lipase B, for an amount of time sufficient to allow release of nucleic acids from the seed, thereby forming a soaked solution comprising nucleic acids;
   c. optionally concentrating and/or purifying the nucleic acids from the soaked solution;
   d. analyzing said soaked solution or said nucleic acids to detect the presence of a nucleic acid of interest; and
   e. optionally, growing a plant from said seed.

25. A method for isolating nucleic acids from small grain cereal seed and/or analyzing a population of small grain cereal seeds comprising the steps of
   a. exposing the endosperm of at least one individual seed of said population;
   b. incubating the seed in an aqueous solution for an amount of time sufficient to allow release of nucleic acids from the seed, thereby forming a soaked solution comprising nucleic acids wherein said aqueous solution for incubating the seeds comprises one or more enzymes selected from the group consisting of pectinase, cellulase, xylanase, amylase, and lipase;
   c. optionally concentrating, amplifying and/or purifying the nucleic acids from the soaked solution;
   d. analyzing said soaked solution or said nucleic acids to detect the presence of a nucleic acid of interest; and
   e. optionally, growing a plant from said seed.

26. The method of claim 25, wherein the endosperm is exposed by treatment with a water jet stream.

\* \* \* \* \*